US007432074B2

(12) United States Patent
Keri et al.

(10) Patent No.: US 7,432,074 B2
(45) Date of Patent: Oct. 7, 2008

(54) METHOD FOR EXTRACTING A MACROLIDE FROM BIOMATTER

(75) Inventors: Vilmos Keri, Debrecen (HU); Lajos Deak, Debrecen (HU); Csaba Szabo, Hajduboszormeny (HU)

(73) Assignee: TEVA Gyógyszergyár Zártkörüen Müködö Részvénytársaság, Debrecen (HU)

( * ) Notice: Subject to any disclaimer, the term of this patent is extended or adjusted under 35 U.S.C. 154(b) by 195 days.

(21) Appl. No.: 10/366,266

(22) Filed: Feb. 12, 2003

(65) Prior Publication Data

US 2003/0166924 A1 Sep. 4, 2003

Related U.S. Application Data

(60) Provisional application No. 60/356,959, filed on Feb. 13, 2002.

(51) Int. Cl.
C12N 1/12 (2006.01)
C12N 1/20 (2006.01)
C12P 1/00 (2006.01)
C12P 1/06 (2006.01)
C12P 7/00 (2006.01)

(52) U.S. Cl. .................. 435/41; 435/132; 435/169; 435/252.1; 435/253.5; 435/898

(58) Field of Classification Search .................. None
See application file for complete search history.

(56) References Cited

U.S. PATENT DOCUMENTS

| 3,993,749 | A |   | 11/1976 | Sehgal et al. |
| 4,160,861 | A |   | 7/1979  | Cole et al. |
| 4,477,682 | A | * | 10/1984 | Tomita et al. ............ 568/362 |
| 4,894,366 | A |   | 1/1990  | Okuhara et al. |
| 5,091,389 | A |   | 2/1992  | Ondeyka et al. |
| 5,116,756 | A |   | 5/1992  | Dumont et al. |
| 5,194,378 | A |   | 3/1993  | Salituro et al. |
| 5,200,505 | A |   | 4/1993  | Takesako et al. |
| 5,264,355 | A |   | 11/1993 | Shaifee et al. |
| 5,494,820 | A |   | 2/1996  | Cullen et al. |
| 5,496,727 | A |   | 3/1996  | Okuhara et al. |
| 5,506,233 | A |   | 4/1996  | Hauske et al. |
| 5,508,398 | A | * | 4/1996  | Gletsos ................ 540/456 |
| 5,612,316 | A |   | 3/1997  | Koch |
| 5,616,595 | A | * | 4/1997  | Chu et al. .............. 514/344 |
| 5,622,866 | A |   | 4/1997  | Motamedi et al. |
| 5,624,842 | A |   | 4/1997  | Okuhara et al. |
| 6,387,258 | B1|   | 5/2002  | Keri et al. |
| 2002/0010328 | A1 |   | 1/2002 | Reeves et al. |
| 2002/0128470 | A1 |   | 9/2002 | Fuenfschilling et al. |
| 2003/0166924 | A1 |   | 9/2003 | Keri et al. |
| 2004/0050782 | A1 |   | 3/2004 | Fuenfschilling et al. |

FOREIGN PATENT DOCUMENTS

| CH | 692 839 A5 | 11/2002 |
| DE | 2121517 | 11/1972 |
| EP | 0 184 162 | 6/1986 |
| EP | 0 652 219 A1 | 5/1995 |
| EP | 1 234 833 A2 | 8/2002 |
| GB | 2 225 576 A | 6/1990 |
| JP | 4128289 | 4/1992 |
| WO | WO 92/18506 | 10/1992 |
| WO | WO 00/33878 | 6/2000 |
| WO | WO-00/71546 | 11/2000 |
| WO | WO-01/18007 A2 | 3/2001 |

OTHER PUBLICATIONS

The Merck Index, Maryadele J. O'Neil et al. eds., "Pimecrolimus", p. 1331, 13th ed. 2001.
Martindale: The complete drug reference, Sean C. Sweetman ed., "Sirolimus", p. 568, Pharmaceutical Press 33rd ed. 2002.
C.E.M. Griffiths "Ascomycin: An Advance in the Management of Atopic Dermatitis" British J. of Dermatology, V. 144, p. 679-681, (2001).
Martindale: The complete drug reference, Sean C. Sweetman ed., "Everolimus", p. 539, Pharmaceutical Press 33rd ed. 2002.
Zhiguo Song et al. "Highly Chemoselective Trichloracetimidate-Mediated Alkylation of Ascomycin: A Convergent, Practical Synthesis of the Immunosupporessant L-733,725" J. Org. Chem. 1999, v. 64, p. 1859-1867.
Jun'ichi Kobayashi et al. "Amphidinolides T2, T3, and T4, New 19-Membered Macrolides from the Dinoflagellate Amphidinium sp. and the Biosynthesis of Amphidinolide T1" J. Org. Chem. 2001, v. 66, p. 134-142.
K. Yoshii et al. "Liquid Chromatographic Determination of Emamectin, Milbemectin, Ivermectin and Abamectin in Crops and Confirmation by Liquid Chromatography—Mass Spectrometry" Journal of Chromatography A, v. 896, 2000, p. 75-85.
Patent Abstract of Japan Publication No. 02016662; Publication date Jan. 19, 1990; Akashi Kazuya "Substituting Terminal Controller".
Surjit S. Sengha, Fermentation, in Kirk Othmer Encyclopedia of Chemical Technology, vol. 10, p. 361-381 (Jacquiline I. Kroschwitz, editor. 4th ed. 1993).
Aceto Pharma GmbH letter to European Patent Office, "'Observations by Third Party' in accordance with Art. 115 EPC regarding European patent application No. 03709066.9", Aug. 27, 2004.
Arndt, Cristl, et al., "Secretion of FK506/FK520 and rapamycin by *Streptomyces* inhibits the growth of competing *Saccharomyces cerevisiae* and *Cryptococcus neoformans*", Microbiology, 1999, vol. 145, pp. 1989-2000.
Akashi, Takeshi, et al., "Quantitative determination of tautomeric FK506 by reversed-phase liquid chromatography", Journal of Pharmaceutical and Biomedical Analysis, 1996, vol. 14, pp. 339-346.
Volosov, Andrew, et al., "Simultaneous simple and fast quantification of three major immunosuppressants by liquid chromatography—tandem mass-spectrometry", Clinical Biochemistry, 2001, vol. 34, pp. 285-290.
Venkataramanan, Raman, et al., "Clinical Utility of Monitoring Tacrolimus Blood Concentrations in Liver Transplant Patients", Journal of Clinical Pharmacology, 2001, vol. 41, pp. 542-551.

(Continued)

*Primary Examiner*—David M. Naff
*Assistant Examiner*—Deborah K. Ware
(74) *Attorney, Agent, or Firm*—Kenyon & Kenyon LLP

(57) ABSTRACT

Provided is a method for obtaining a macrolide, especially tacrolimus, from biomatter.

24 Claims, No Drawings

OTHER PUBLICATIONS

Motamedi, Haideh, et al., "Structural organization of a multifunctional polyketide synthase involved in the biosynthesis of the macrolide immunosuppressant FK506", European Journal of Biochemistry, Feb. 1997, vol. 244, No. 1, pp. 74-80.

Motamedi, Haideh, et al., "The biosynthetic gene cluster for the macrolactone ring of the immunosuppressant FK506", European Journal of Biochemistry, 1998, vol. 256, pp. 528-5343.

Aichi, Ken, et a., "Studies on the Development of Tacrolimus Production", Seibutsu Kogaku Kaishi, 1998, vol. 76, No. 9, pp. 389-397.

Shafiee, Ali, et al., "Enzymology of FK506 biosynthesis: Purification and characterization of 31-O-desmethylFK-506 O: methyltransferase from *Streptomyces* sp. MA6858", European Journal of Biochemistry, Oct. 1994, vo. 225, No. 2, pp. 755-764.

Motamedi, Haideh, et al., "Characterization of Methyltransferase and Hydroxylase Genes Involved in the Biosynthesis of the Immunosuppressants FK506 and FK520", Journal of Bacteriology, Sep. 1996, vol. 178, No. 17, pp. 5243-5248.

Schwecke, Torsten, et al., "The biosynthetic gene cluster for the polyketide immunosuppressant rapamycin", Proc. Natl. Acad. Sci. USA, Aug. 1995, vol. 95, pp. 7839-7843.

Wu, Kai, et al., "The FK520 gene cluster of *Streptomyces hygroscopicus* var. *ascomyceticus* (ATCC 14891) contains genes for biosynthesis of unusual polyketide extender units", Gene, 2000, vol. 251, pp. 81-90.

Kino, Toru, et al., "FK-506, A novel Immunosuppressant Isolated From A *Streptomyces*: I. Fermentation, Isolation, and Physico-Chemical and Biological Characteristics", The Journal of Antibiotics, vol. XL, No. 9, pp. 1249-1255.

Yoon, Yeo Joon, et al., "Nutrient Effects on FK-506, a New Immunosuppressant, Production by *Streptomyces* sp. in a Defined Medium", Journal of Fermentation and Bioengineering, 1997, vol. 83, No. 6, pp. 599-603.

Takeuchi, Miwako, et al., "Ring-closing metathesis protocol for a diastereocontrolled preparation of the $C_{28}$-$C_{34}$ segment of FK-506", Tetrahedron: Asymmetry, 2000, vol. 11, pp. 1601-1606.

Namyslo, Jan-Christoph, et al., "An Aldol Approach to a Building Block corresponding to the C21-C26-Part of FK506", J. Prakt. Chem., 1999, vol. 341, No. 6, pp. 557-561.

Baker, Robert K., et al., "Synthetic Studies on the Immunosuppressive Agent FK-506: Enantioselective Synthesis of a C22-C34 Fragment", Tetrahedron Letters, 1998, vol. 39, pp. 229-232.

Morimoto, Yoshiki, et al., "A Synthesis of C1-C22 Fragment of the Immunosuppressant FK506. Stereoselective Construction of ($E$)-Trisubstituted Double Bond (C19-C20) via Ester-enolate Claisen Rearrangement", Tetrahedron Letters, 1991, vol. 32, No. 25, pp. 2909-2912.

Marshall, James A., et al., "Synthesis of a C22-34 Subunit of the Immunosuppressant FK-506", Journal of Organic Chemistry, 1996, vol. 60, pp. 7230-7237.

Ireland, Robert E., et al., "A Total Synthesis of FK-506", Journal of Organic Chemistry, 1996, vol. 61, pp. 6856-6872.

Ireland, Robert E., et al., "Total Synthesis of FK-506. Part 1: Construction of the C16-C34 Fragment", Tetrahedron, 1997, vol. 53, No. 39, pp. 13221-13256.

Ireland, Robert E., et al., "Total Synthesis of FK-506. Part 2. Completion of the Synthesis", Tetrahedron, 1997, vol. 53, No. 39, pp. 13257-13284.

Smith, Amos B., et al., "Formal Total Synthesis of FK506. Concise Consttruction of the C(10)-C(34) Segment Via an Effective Coupling Tactic", Tetrahedron Letters, 1994, vol. 35, No. 25, pp. 4271-4274.

Nakatsuka, Masashi, et al., "Total Synthesis of FK506 and an FKBP Probe Reagent, ($C_8$, $C_9$-$^{13}C_2$)-FK506", Journal of the American Chemical Society, 1990, vol. 112, pp. 5583-5601.

Jones, Todd K., et al., "Total Synthesis of the Immunosuppressant (−)-FK-506", Journal of the American Chemical Society, 1989, vol. 111, pp. 1157-1159.

* cited by examiner

METHOD FOR EXTRACTING A MACROLIDE FROM BIOMATTER

CROSS REFERENCE TO RELATED APPLICATION

This application claims the benefit under 35 U.S.C. §1.119(e) of Provisional Application Ser. No. 60/356,959, filed Feb. 13, 2002, and is incorporated herein by reference.

FIELD OF THE INVENTION

The present invention relates to a method of extracting a macrolide, for example tacrolimus, from biomatter, especially fermentation broth.

BACKGROUND OF THE INVENTION

Macrolides are multi-membered lactone rings having one or more deoxy sugars as substituents. Erythromycin, azithromycin, and clarithromycin are macrolides that have bacteriostatic and/or bactericidal activity.

Tacrolimus (FK 506) is also a macrolide antibiotic that is also an immunosuppressive agent. More potent than cyclosporin, tacrolimus has a selective inhibitory effect on T-lymphocytes.

The macrolides are typically obtained by fermentation, although synthetic routes to some are known. The present extraction method offers several advantages over the prior art. For example, the entire fermentation broth can be used as starting material for the present method ("whole broth method") and the use of hydrophobic extraction solvent results in an efficient extraction yield, leaving behind most water-soluble impurities, with removal of mycelium in one step. Concentration under reduced pressure at temperature above 25° C. and reduced pressure results in a high evaporation rate of solvent without precipitation or decomposition of tacrolimus. Further advantages of the present invention will be apparent to the skilled artisan.

SUMMARY OF THE INVENTION

In one aspect, the present invention relates to a method for obtaining a macrolide, especially tacrolimus, including the step of extracting macrolide-containing biomatter with a hydrophobic extraction solvent, especially wherein the hydrophobic extraction solvent is selected from the group consisting of n-butanol, iso-butanol, $C_2$-$C_6$ linear and branched esters of acetic acid or formic acid, $C_3$-$C_6$ linear or branched aliphatic ketones, halogenated methanes, halogenated ethanes, and aromatic hydrocarbons that are liquid at 25° C. and that have a boiling point at atmospheric pressure less than about 150° C., to obtain a solution of the macrolide in the hydrophobic extraction solvent, wherein the pH of the biomatter being extracted is about 5.5 to about 13.

In another aspect, the present invention relates to a method for obtaining a macrolide, especially tacrolimus, including the step of extracting macrolide-containing biomatter with a hydrophobic extraction solvent, especially wherein the hydrophobic extraction solvent is selected from the group consisting of n-butanol, iso-butanol, $C_2$-$C_6$ linear and branched esters of acetic acid or formic acid, $C_3$-$C_6$ linear or branched aliphatic ketones, halogenated methanes, halogenated ethanes and aromatic hydrocarbons that are liquid at 25° C. and that have a boiling point at atmospheric pressure less than about 150° C., wherein the extraction is at a temperature between about 2° C. to about 70° C., especially between about 15° C. and about 35° C., to obtain a solution of the macrolide in the hydrophobic extraction solvent.

In a further aspect, the present invention relates to a method for obtaining a macrolide, especially tacrolimus, including the step of extracting macrolide-containing biomatter with a hydrophobic extraction solvent, especially wherein the hydrophobic extraction solvent is selected from the group consisting of n-butanol, iso-butanol $C_2$-$C_6$ linear and branched esters of acetic acid or formic acid, $C_3$-$C_6$ linear or branched aliphatic ketones, halogenated methanes, halogenated ethanes, and aromatic hydrocarbons that are liquid at 25° C. and that have a boiling point at atmospheric pressure less than about 150° C., wherein the extraction is at a temperature between about 2° C. to about 70° C., especially between about 15° C. and about 35° C., and at a pH of between about 5.5 and about 13, especially between about 7.5 and about 13, to obtain a solution of the macrolide in the hydrophobic extraction solvent.

In a further aspect, the present invention relates to a method for obtaining a macrolide, especially tacrolimus, including the steps of extracting macrolide-containing biomatter with a hydrophobic extraction solvent, especially wherein the hydrophobic extraction solvent is selected from the group consisting of n-butanol, iso-butanol, $C_2$-$C_6$ linear and branched esters of acetic acid or formic acid, $C_3$-$C_6$ linear or branched aliphatic ketones, halogenated methanes, halogenated ethanes, and aromatic hydrocarbons that are liquid at 25° C. and that have a boiling point at atmospheric pressure less than about 150° C., wherein the extraction is at a temperature between about 2° C. to about 70° C., especially between about 15° C. and about 35° C., and at a pH of between about 5.5 and about 13, especially between about 7.5 and about 13, to obtain a solution of the macrolide in the hydrophobic extraction solvent, concentrating the macrolide-containing solution, treating the concentrated solution by column chromatigraphy to obtain at least one macrolide-containing fraction that is a macrolide-containing solution, and crystallizing the macrolide from the solution.

In yet another aspect, the present invention relates to a method for obtaining a macrolide, especially tacrolimus, including the steps of extracting macrolide-containing biomatter with a hydrophobic extraction solvent, especially wherein the hydrophobic extraction solvent is selected from the group consisting of n-butanol, iso-butanol, $C_2$-$C_6$ linear and branched esters of acetic acid or formic acid, $C_3$-$C_6$ linear or branched aliphatic ketones, halogenated methanes, halogenated ethanes, and aromatic hydrocarbons that are liquid at 25° C. and that have a boiling point at atmospheric pressure less than about 150° C., to obtain a solution of the macrolide in the hydrophobic extraction solvent, separating the solution containing the macrolide from the extracted macrolide-containing biomatter, concentrating the separated macrolide-containing solution, treating the concentrated solution by column chromatography to obtain at least one macrolide-containing fraction that is a macrolide-containing solution, optionally concentrating the solution, and crystallizing the macrolide from the optionallyconcentrated separated solution by cooling, especially to a temperature of about 20° C. or less, and isolating the crystallized macrolide.

In yet another aspect, the present invention relates to a method for obtaining a macrolide, especially tacrolimus, including the steps of extracting macrolide-containing biomatter with a hydrophobic extraction solvent, especially wherein the hydrophobic extraction solvent is selected from the group consisting of n-butanol, iso-butanol, $C_2$-$C_6$ linear and branched esters of acetic acid or formic acid, $C_3$-$C_6$ linear or branched aliphatic ketones, halogenated methanes, halogenated ethanes, and aromatic hydrocarbons that are liquid at 25° C. and that have a boiling point at atmospheric pressure less than about 150° C., to obtain a solution of the macrolide in the hydrophobic extraction solvent, separating the solution containing the macrolide from the extracted macrolide-containing biomatter, concentrating the separated macrolide-containing solution, treating the concentrated solution by column chromatography to obtain at least one macrolide-containing fraction that is a macrolide-containing solution, optionally concentrating the solution, and crystallizing the macrolide from the optionally concentrated separated solution by combining the concentrated separated solution with a crystallization solvent selected from acetonitrile, methanol, ethanol, acetone, diethyl ether, ethyl acetate, the hexanes, the heptanes, and water, and isolating the crystallized macrolide.

In still a further aspect, the present invention relates to a method of obtaining a macrolide, especially tacrolimus, including the step of extracting macrolide containing biomatter obtained from a microorganism selected form *Streptomyces tsukubaensis, Streptomyces hygroscopicus*, and *Streptomyces lividans*, with a hydrophobic extraction solvent, wherein the hydrophobic extraction solvent is selected from the group consisting of n-butanol, iso-butanol, $C_2$-$C_6$ linear and branched esters of acetic acid or formic acid, $C_3$-$C_6$ linear or branched aliphatic ketones, halogenated methanes, halogenated ethanes, and aromatic hydrocarbons that are liquid at 25° C. and that have a boiling point at atmospheric pressure less than about 150° C., to obtain a solution of the macrolide in the hydrophobic extraction solvent, wherein the pH of the bimatter extracted is about 5.5 to about 13.

In yet another aspect, the present invention relates to a method of obtaining tacrolimus from tacrolimus-containing biomatter including the steps of: extracting tacrolimus-containing biomatter that is whole fermentation broth obtained by fermentation of a microorganism selected from the group consisting of *Streptomyces tsukubaensis, Streptomyces hygroscopicus*, and *Streptomyces lividans*, with a hydrophobic extraction solvent selected form the group consisting of n-butyl acetate, isobutyl acetate, t-butyl acetate, ethyl acetate, propyl acetate, ethyl formate, butyl methyl ketone, dichloromethane, chloroform, tetrachloromethane, and toluene at a temperature between about 2° C. and about 70° C., especially between about 15° C. and about 35° C. at a pH between about 5.5 and about 13, especially between about 7.5 and about 13 to obtain a solution of tacrolimus in the hydrophobic extraction solvent; separating the tacrolimus-containing solution from the extracted tacrolimus-containing biomatter; concentrating the tacrolimus-containing solution; treating the concentrated solution by column chromatography to obtain at least one macrolide-containing fraction that is a macrolide-containing solution, optionally concentrating the solution, and crystallizing the tacrolimus from the optionally concentrated separated solution by cooling it or by combining it with a crystallization solvent selected from acetonitrile, methanol, ethanol, acetone, diethyl ether, ethyl acetate, the hexanes, the heptanes, and water, whereby a precipitate of crystallized tacrolimus is formed; and separating tacrolimus.

In still yet another embodiment, the present invention relates to a method of obtaining tacrolimus from tacrolimus-containing biomatter including the steps of: extracting tacrolimus-containing biomatter that is whole fermentation broth obtained by fermentation of a microorganism selected from the group consisting of *Streptomyces tsukubaensis, Streptomyces hygroscopicus*, and *Streptomyces lividans*, with a iso-butyl acetate, at a temperature between about 2° C. and about 70° C., especially between about 15° C. and about 35° C., to obtain a solution of tacrolimus in iso-butyl acetate solvent; separating the tacrolimus-containing iso-butyl acetate solution from the extracted tacrolimus-containing biomatter; concentrating the tacrolimus-containing iso-butyl acetate solution; treating the concentrated solution by column chromatography to obtain at least one macrolide-containing fraction that is a macrolide-containing solution, optionally concentrating the solution, and crystallizing the tacrolimus from the optionally concentrated separated solution by cooling it to a temperature of about 20° C. or less, or by combining it with a crystallization solvent selected from acetonitrile, methanol, ethanol, acetone, diethyl ether, ethyl acetate, the hexanes, the heptanes, and water, whereby a precipitate of crystallized tacrolimus is formed; and separating tacrolimus.

DETAILED DESCRIPTION OF THE INVENTION

In one embodiment, the present invention provides a method for obtaining a macrolide, preferably tacrolimus (also known as FK 506), from macrolide-containing biomatter that includes the step of extracting the macrolide from the macrolide-containing biomatter with a hydrophobic extraction solvent to obtain a solution of the macrolide in the hydrophobic extraction solvent, wherefrom the macrolide can be obtained. In another embodiment, the present invention provides a method for obtaining a macrolide, preferably tacrolimus, from macrolide-containing biomatter by extracting the biomatter with a hydrophobic extraction solvent to obtain a solution of the macrolide followed by concentration of the solution to obtain a concentrate, wherefrom the macrolide is isolated.

Macrolide-containing biomatter is matter obtained from or through use of a macrolide-producing microorganism, for example bacteria or fungus that produces macrolide by fermentation or culturing or the like. Fermentation of microorganism can be carried out by methods well known to the skilled artisan and described, for example, in Surjit S. Sengha, Fermentation, in 10 *Kirk Othmer Encyclopedia of Chemical Technology*, 361 (Jacquiline I. Kroschwitz, ed. 4$^{th}$ ed. 1993).

Preferred macrolide-containing biomatter is tacrolimus-containing biomatter, particularly fermentation broth obtainable by fermentation using a tacrolimus-producing microorganism, for example, *Streptomyces tsukubaensis*, new and mutated strains thereof, *Streptomyces hygroscopicus*, and *Streptomyces lividans*, as described in U.S. Pat. Nos. 4,894, 366, 5,116,756, 5,624,842, 5,496,727, and 5,622,866.

Mycelium and filtrate obtained by filtration of fermentation broth from fermentation of a macrolide-producing microorganism are also biomatter useful in the practice of the present invention. The entire fermentation broth, i.e. "whole broth" from fermentation of a macrolide-producing microorganism, unfiltered or purified to separate mycelium, is a preferred macrolide-containing biomatter for the practice of the present invention. When whole broth is used, the present method can be referred to as a "whole-broth method".

The macrolide-containing biomatter is extracted with a hydrophobic extraction solvent that is a solvent for the macrolide, especially tacrolimus, but that is only sparingly soluble in water at 25° C. Preferred hydrophobic extraction solvents are $C_2$-$C_6$ linear and branched esters of acetic acid or formic acid, for example iso-butyl acetate, $C_3$-$C_6$ linear or branched aliphatic ketones, halogenated methanes, for example dichloromethane, halogenated ethanes, for example dichloroethane, and aromatic hydrocarbons that are liquid at 25° C. and that have a boiling point at atmospheric pressure less that about 150° C. Normal and iso-butyl alcohols can also be used as the hydrophobic extraction solvent.

Preferred as hydrophobic extraction solvents are iso-butyl acetate, n-butyl acetate, t-butyl acetate, ethyl acetate, propyl acetate, ethyl formate, butyl methyl ketone (2-hexanone), dichloromethane, chloroform, tetrachloromethane, and toluene.

Ethyl acetate and iso-butyl acetate are particularly preferred hydrophobic extraction solvents.

The extraction to form a solution of the macrolide can be performed using such methods and equipment as are known to skilled artisan and routiner alike. The method and equipment chosen must only provide adequate agitation and allow for separation of the solution from extracted macrolide-containing biomatter, or for transfer of the extraction mixture to a separation device. Extraction can be carried out at any convenient temperature between about 2° C. and about 70° C. Preferably, the extraction is carried out at a temperature between about 15° C. and about 35° C. The skilled artisan will know to optimize the extraction time depending on the macrolide-containing biomatter, hydrophobic extraction solvent, equipment, and temperatures used. At the end of the extraction, the extraction mixture includes a solution of the macrolide in the hydrophobic extraction solvent as well as residual extracted macrolide-containing biomatter.

In a preferred embodiment, the extraction is performed on biomatter, for example fermentation broth, that is not first subjected to any purification treatment, for example filtration that would remove mycelium. In this case, the extraction is referred to as whole broth extraction.

The extraction can be performed at any pH between about 1 and about 13. Preferably, the extraction is conducted at a pH between about 5.5 and about 13, most preferably between about 7.5 and about 13. The pH of the biomatter, especially fermentation broth, can be adjusted using a suitable inorganic base, for example $NH_4OH$, NaOH, KOH, LiOH, or $Ca(OH)_2$, to mention just a few. The present inventors have observed particular advantages, especially in regards to the purity of macrolide, when the extraction is carried-out on biomatter having a pH between about 5.5 and about 13. Preferably, the pH is an alkaline pH, especially a pH between about 7.5 and about 13.

Following extraction, the solution of macrolide in hydrophobic extraction solvent is separated from the extraction mixture and, in preferred embodiments, concentrated to obtain a concentrate. The separation can be accomplished using methods and equipment well known to skilled artisan and routiner alike, for example decanting, separating in a separatory funnel, and centrifuging using a liquid-liquid centrifuge.

The macrolide-containing solution separated from extracted macrolide-containing biomatter is concentrated to obtain a concentrate. The concentration can be at prevailing atmospheric pressure (which the skilled artisan recognizes varies slightly about a mean of 760 mm Hg), or it can be at reduced pressure, attained with the aid of, for example, a vacuum pump or water aspirator. The concentration is preferably carried out at a temperature above about 25° C. The concentration is carried out until the volume of the macrolide-containing solution is reduced to about 0.2 to about 2.0 percent of its initial volume, or less to provide concentrated macrolide-containing solutions ("concentrate"). Crude tacrolimus can be isolated from the concentrate.

In preferred embodiments, the concentrate is treated by column chromatography on a silica gel column. The chromatography method applied can be that described in U.S. Pat. No. 4,894,366, incorporated herein in its entirety by reference.

For treatment, concentrate (concentrated macrolide-containing solution) is loaded onto a silica gel column. For loading, the concentrate can be combined with a solvent that is a solvent for the macrolide, for example ethyl acetate, and slurried with silica gel. Solvent is removed from the slurry to afford silica gel loaded with macrolide and other substances from the concentrate. The loaded silica gel is charged to the top of the column and, if desired, a loading eluent is passed through the column. The column is then eluted with an eluent.

The eluent can be isochratic, that is of constant composition, or the composition of the eluent can be varied during elution. Preferred eluents include mixtures of ethyl acetate and hexane.

Fractions are collected to obtain at least one macrolide-containing fraction that is a solution of macrolide in eluent. Multiple macrolide-containing fractions can be combined to a sinfle macrolide-containing fraction. The macrolide-containing fraction(s) can be concentrated to obtain a concentrated solution (concentrated fraction) of macrolide, wherefrom the macrolide can be crystallized.

The macrolide is crystallized (precipitated) from the preferably concentrated macrolide-containing solution. Macrolide so crystallized (precipitated) can be isolated by, for example, filtration or centrifugation. Crystallization can be effected by cooling the macrolide-containing solution, preferably to temperature of about 20° C. or less. Crystallization can also be effected with the aid of a crystallization solvent that is combined with the preferably concentrated macrolide-containing solution. In preferred embodiments, the combination is thereafter maintained for a holding period of about 10 to about 60 hours at a temperature of about 25° C. or below. The typical hold time is 48 hours. Useful crystallization solvents include acetonitrile, methanol, ethanol, acetone, diethyl ether, ethyl acetate, hexanes, heptanes, and water.

In particular embodiments, the macrolide-containing solution is concentrated to dryness and the macrolide is obtained without further cooling and without use of a crystallization solvent.

The practice of the invention is further illustrated with the following non-limiting examples.

EXAMPLE 1

Fermentation broth (50 ml) was mixed with 50 ml iso-butyl acetate. The pH of the mixture was adjusted to pH 2 with diluted sulfuric acid solution. After 30 minutes stirring, phases were separated. The separated iso-butyl acetate phase (39 ml) was concentrated to dryness under reduced pressure at 60° C. The achieved yield was 83%.

EXAMPLE 2

Fermentation broth (50 ml) was mixed with 50 ml iso-butyl acetate. Magnesium sulfate of 250 mg and some drops of diluted dodecyl trimethyl ammonium chloride solution were added to the mixture. The pH of the mixture was adjusted to pH 4 with diluted sulfuric acid solution. After 30 minutes stirring, phases were separated. The separated iso-butyl acetate phase (44 ml) was concentrated to dryness under reduced pressure at 70° C. The achieved yield was 88%.

EXAMPLE 3

Fermentation broth (50 ml) was mixed with 50 ml iso-butyl acetate. Magnesium sulfate of 250 mg and some drops of diluted dodecyl trimethyl ammonium chloride solution were added to the mixture. The pH of the mixture was adjusted to pH 8 with diluted sodium hydroxide solution. The combination was heated to 35-40° C. Phases were separated after 30 minutes stirring. The iso-butyl acetate phase (44 ml) was concentrated to dryness under reduced pressure at 82° C. The achieved yield was 94%.

EXAMPLE 4

Fermentation broth (50 ml) was mixed with 50 ml iso-butyl acetate. Magnesium sulfate of 250 mg and some drops of diluted dodecyl trimethyl-ammonium chloride solution were added to the mixture. The pH of the mixture was adjusted to pH 10 with diluted sodium hydroxide solution. The combination was cooled to 15° C. Phases were separated after 30 minutes stirring. The iso-butyl acetate phase (43 ml) was concentrated to dryness under reduced pressure at 55° C. The achieved yield was 92%.

EXAMPLE 5

Fermentation broth (50 ml) was mixed with 50 ml ethyl acetate. Magnesium sulfate of 250 mg and some drops of diluted dodecyl trimethyl ammonium chloride solution were added to the mixture. The pH of the mixture was adjusted to pH 4 with diluted sulfuric acid solution. Phases were separated after 30 minutes stirring. The separated ethyl acetate phase was concentrated to dryness under reduced pressure at 29° C. The achieved yield was 92%.

What is claimed is:

1. A method for obtaining a macrolide comprising the step of extracting macrolide-containing biomatter that is whole fermentation broth with a hydrophobic extraction solvent to obtain a solution of the macrolide in the hydrophobic extraction solvent, wherein the pH of the macrolide-containing biomatter being extracted is between 8 and about 13 and recovering said macrolide from said solution.

2. The method of claim 1 wherein the hydrophobic extraction solvent is selected from the group consisting of n-butanol, iso-butanol, $C_2$-$C_6$ linear and branched esters of acetic acid or formic acid, $C_3$-$C_6$ linear or branched aliphatic ketones, halogenated methanes, halogenated ethanes, and aromatic hydrocarbons that are liquid at 25° C. and that have a boiling point at atmospheric pressure less than about 150° C.

3. The method of claim 2 wherein the hydrophobic extraction solvent is selected from the group consisting of n-butanol, iso-butanol, n-butyl acetate, iso-butyl acetate, t-butyl acetate, ethyl acetate, propyl acetate, ethyl formate, butyl methyl ketone, methyl iso-butyl ketone, dichloromethane, chloroform, tetrachloromethane, dichloroethane, and toluene.

4. The method of claim 3 wherein the hydrophobic extraction solvent is ethyl acetate, iso-butyl acetate, or a mixture of these.

5. The method of claim 4 wherein the hydrophobic extraction solvent is iso-butyl acetate.

6. The method of claim 1 wherein the extraction is at a temperature between about 2° C. and about 70° C.

7. The method of claim 6 wherein the extraction is at a temperature between about 15° C. and about 35° C.

8. The method of claim 1 wherein the pH of the biomatter extracted is between 8 and about 10.

9. The method of claim 1 wherein the macrolide-containing biomatter is obtained from a microorganism selected from *Streptomyces tsukubaensis*, *Streptomyces hygroscopicus*, and *Streptomyces lividans*.

10. The method of claim 1 wherein the macrolide is tacrolimus.

11. The method of claim 10 wherein the pH of the biomatter is between 8 and about 10.

12. The method of claim 11 wherein the hydrophobic extraction solvent is iso-butyl acetate.

13. The method of claim 1 further comprising the steps of, after extraction;
   separating the solution containing the macrolide from the extracted macrolide-containing biomatter to obtain a separated macrolide-containing solution,
   concentrating the separated macrolide-containing solution to form a concentrated macrolide-containing solution,
   loading the concentrated macrolide-containing solution onto a silica gel column and eluting with an eluent to obtain at least one macrolide-containing fraction that is a macrolide-containing solution, and
   isolating the macrolide.

14. The method of claim 1 wherein the pH of the biomatter is between about 10 and about 13.

15. The method of claim 1, wherein macrolide is obtained from a macrolide-containing biomatter and the yield of the macrolide is about 83 % to about 94 %.

16. The method of claim 1 comprising:
   a) extracting macrolide-containing biomatter that is whole fermentation broth obtained by fermentation of a microorganism selected from the group consisting of *Streptomyces tsukubaensis*, *Streptomyces hygroscopicus*, and *Streptomyces lividans* with a hydrophobic extraction solvent selected form the group consisting of n-butanol, iso-butanol, n-butyl acetate, iso-butyl acetate, t-butyl acetate, ethyl acetate, propyl acetate, ethyl formate, butyl methyl ketone, dichloromethane, chloroform, tetrachloromethane, dichloroethane and toluene to obtain a solution of the macrolide in hydrophobic extraction solvent at a temperature between about 2° C. and about 70° C., wherein the macrolide is tacrolimus.

17. The method of claim 16, further comprising the steps of:
   b) isolating the macrolide-containing solution from the extracted macrolide-containing biomatter,
   c) concentrating the macrolide-containing solution,
   d) purifying the concentrated macrolide-containing solution on a silica gel chromatography column.

18. The method of claim 16 wherein the pH of the whole fermentation broth is between 8 and about 10.

19. The method of claim 16 wherein the hydrophobic extraction solvent is iso-butyl acetate.

20. The method of claim 16 wherein the extraction is at a temperature between about 15° C. and about 30° C.

21. A method of obtaining a macrolide from a macrolide-containing biomatter comprising the steps of:
   a) extracting macrolide-containing biomatter that is whole fermentation broth obtained by fermentation of a microorganism selected from the group consisting of *Streptomyces tsukubaensis*, *Streptomyces hygroscopicus*, and *Streptomyces lividans* with iso-butyl acetate wherein the pH of the macrolide-containing biomatter is between 8 and about 13 to obtain a solution of a macrolide in iso-butyl acetate at a temperature between about 2° C. and about 70° C., b) isolating the macrolide-containing solution from the extracted macrolide-containing biomatter,
c) concentrating the macrolide-containing solution,
d) purifying the concentrated macrolide-containing solution on a silica gel chromatography column to obtain at least one macrolide-containing fraction that is a macrolide-containing solution,
e) concentrating at least one macrolide-containing fraction, wherein the macrolide is tacrolimus, and
(f) recovering said tacrolimus from step (e).

22. The method of claim 21 wherein the pH of the macrolide-containing biomatter is between 8 and about 10.

23. The method of claim 21 wherein the temperature of extraction is between about 15° C. and about 35° C.

24. The method of claim 21, wherein macrolide is obtained from a macrolide-containing biomatter and the yield of the macrolide is about 83% to about 94%.

* * * * *